United States Patent
Choi et al.

(10) Patent No.: US 10,048,180 B2
(45) Date of Patent: Aug. 14, 2018

(54) COATING BOND TEST METHOD AND METHOD OF MAKING A SPECIMEN FOR TESTING BOND STRENGTH OF A COATING

(71) Applicant: Sikorsky Aircraft Corporation, Stratford, CT (US)

(72) Inventors: JinKyu Choi, Trumbull, CT (US); Rajiv A. Naik, Glastonbury, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 0 days.

(21) Appl. No.: 15/519,185

(22) PCT Filed: Oct. 16, 2015

(86) PCT No.: PCT/US2015/055973
§ 371 (c)(1),
(2) Date: Apr. 14, 2017

(87) PCT Pub. No.: WO2016/061477
PCT Pub. Date: Apr. 21, 2016

(65) Prior Publication Data
US 2017/0234784 A1    Aug. 17, 2017

Related U.S. Application Data

(60) Provisional application No. 62/064,568, filed on Oct. 16, 2014.

(51) Int. Cl.
*G01N 3/08* (2006.01)
*G01N 19/04* (2006.01)

(52) U.S. Cl.
CPC .............. *G01N 3/08* (2013.01); *G01N 19/04* (2013.01); *G01N 2203/0017* (2013.01);
(Continued)

(58) Field of Classification Search
CPC ... G01N 2203/0017; G01N 2203/0268; G01N 2203/0067; G01N 2203/0091; G01N 2203/0096; G01N 3/08; G01N 19/04
(Continued)

(56) References Cited

U.S. PATENT DOCUMENTS 4,548,083 A    10/1985    Schuerer
4,586,371 A    5/1986    Ivie et al.
(Continued)

FOREIGN PATENT DOCUMENTS

JP    S5866837 A    4/1983
WO    2004023111 A1    3/2004

OTHER PUBLICATIONS

International Search Report and Written Opinion of the International Search Authority dated Jan. 4, 2016 in related PCT Application No. PCT/US2015/055973, 6 pages.
(Continued)

*Primary Examiner* — Jonathan Dunlap
(74) *Attorney, Agent, or Firm* — Cantor Colburn LLP

(57) ABSTRACT

A coating bond test method includes, attaching with an adhesive a pull-off bar to a coating on a planar surface of a substrate for which a normal bond strength between the coating and the substrate is sought, reducing a first area defined by an interface between the substrate and the coating to a value less than a second area defined by an interface between the adhesive and the coating, urging the pull-off bar away from the substrate in a direction normal to the planar surface until failure occurs, and recording a load at which failure occurred.

16 Claims, 2 Drawing Sheets

(52) U.S. Cl.
CPC ............... *G01N 2203/0067* (2013.01); *G01N 2203/0091* (2013.01); *G01N 2203/0096* (2013.01); *G01N 2203/0268* (2013.01)

(58) Field of Classification Search
USPC .......... 73/150 R, 150 A, 826, 827, 830, 828, 73/841, 842
See application file for complete search history.

(56) References Cited

U.S. PATENT DOCUMENTS

| | | | | |
|---|---|---|---|---|
| 4,606,225 A * | 8/1986 | Thomason | ............. | G01N 19/04 73/150 A |
| 4,993,268 A * | 2/1991 | Thompson | ............... | G01N 3/08 73/827 |
| 5,768,936 A | 6/1998 | Mann | | |
| 6,117,695 A | 9/2000 | Murphy | | |
| 6,176,141 B1 | 1/2001 | Chuang et al. | | |
| 6,282,950 B1 | 9/2001 | Taylor, Jr. et al. | | |
| 6,289,741 B1 | 9/2001 | Ghetzler | | |
| 6,393,905 B1 | 5/2002 | Steele | | |
| 7,448,279 B2 * | 11/2008 | Brinz | ....................... | G01N 3/08 73/150 A |
| 7,497,115 B2 * | 3/2009 | Menendez Martin | . | G01N 19/04 73/150 A |
| 7,669,467 B2 * | 3/2010 | Breuer | ................. | F16B 11/006 73/150 A |
| 7,739,918 B1 | 6/2010 | Lapeyronnie | | |
| 8,096,190 B2 * | 1/2012 | Rey | ......................... | G01N 19/04 264/260 |
| 8,387,467 B2 * | 3/2013 | Bassot | ..................... | G01N 3/56 427/478 |
| 8,677,813 B2 | 3/2014 | Sellars et al. | | |
| 8,707,798 B2 * | 4/2014 | Gregg | .................... | G01N 19/04 73/150 A |
| 2005/0193829 A1 * | 9/2005 | Brinz | ....................... | G01N 3/08 73/794 |
| 2006/0159513 A1 * | 7/2006 | Breuer | ................. | F16B 11/006 403/27 |
| 2007/0228591 A1 * | 10/2007 | Rey | ......................... | G01N 19/04 264/40.1 |
| 2008/0011075 A1 * | 1/2008 | Menendez Martin | . | G01N 19/04 73/150 A |
| 2011/0138926 A1 * | 6/2011 | Bassot | ..................... | G01N 3/56 73/826 |
| 2011/0214497 A1 * | 9/2011 | Sellars | ................... | G01N 19/04 73/150 A |
| 2013/0340534 A1 * | 12/2013 | Gregg | .................... | G01N 19/04 73/826 |

OTHER PUBLICATIONS

Extended European Search Report for EP Application No. 15850011.6, dated Jun. 7, 2018, 9 pages.

* cited by examiner

COATING BOND TEST METHOD AND METHOD OF MAKING A SPECIMEN FOR TESTING BOND STRENGTH OF A COATING

CROSS-REFERENCE TO RELATED APPLICATIONS

The present application is a 371 National Stage of International Patent Application No. PCT/US2015/055973, filed on Oct. 16, 2015, which claims priority to U.S. Provisional Application No. 62/064,568, filed on Oct. 16, 2014, the contents of which are incorporated herein by reference in their entirety.

BACKGROUND OF THE INVENTION

The bond strength of coatings, such as thermal spay coatings, is of interest to those who use as well as those who develop these coatings. One current method of evaluating the bond strength of coating is test method ASTM-C633. The bond strength of some coatings, however, is too great to be measured with this test, due to failures that occur on test specimens in locations other than at the desired bond location. The industry would therefore be receptive to new test methods that allow for evaluation of the bond location of interest.

BRIEF DESCRIPTION OF THE INVENTION

Disclosed herein is a coating bond test method. The method includes, attaching with an adhesive a pull-off bar to a coating on a planar surface of a substrate for which a normal bond strength between the coating and the substrate is sought, reducing a first area defined by an interface between the substrate and the coating to a value less than a second area defined by an interface between the adhesive and the coating, urging the pull-off bar away from the substrate in a direction normal to the planar surface until failure occurs, and recording a load at which failure occurred.

Further disclosed herein is a method of making a specimen for testing bond strength of a coating. The method includes, forming a substrate with a planar surface, applying a coating to the planar surface, attaching with adhesive a pull-off bar to the coating, and reducing a first area defined by an interface between the substrate and the coating to a value less than a second area defined by an interface between the adhesive and the coating.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
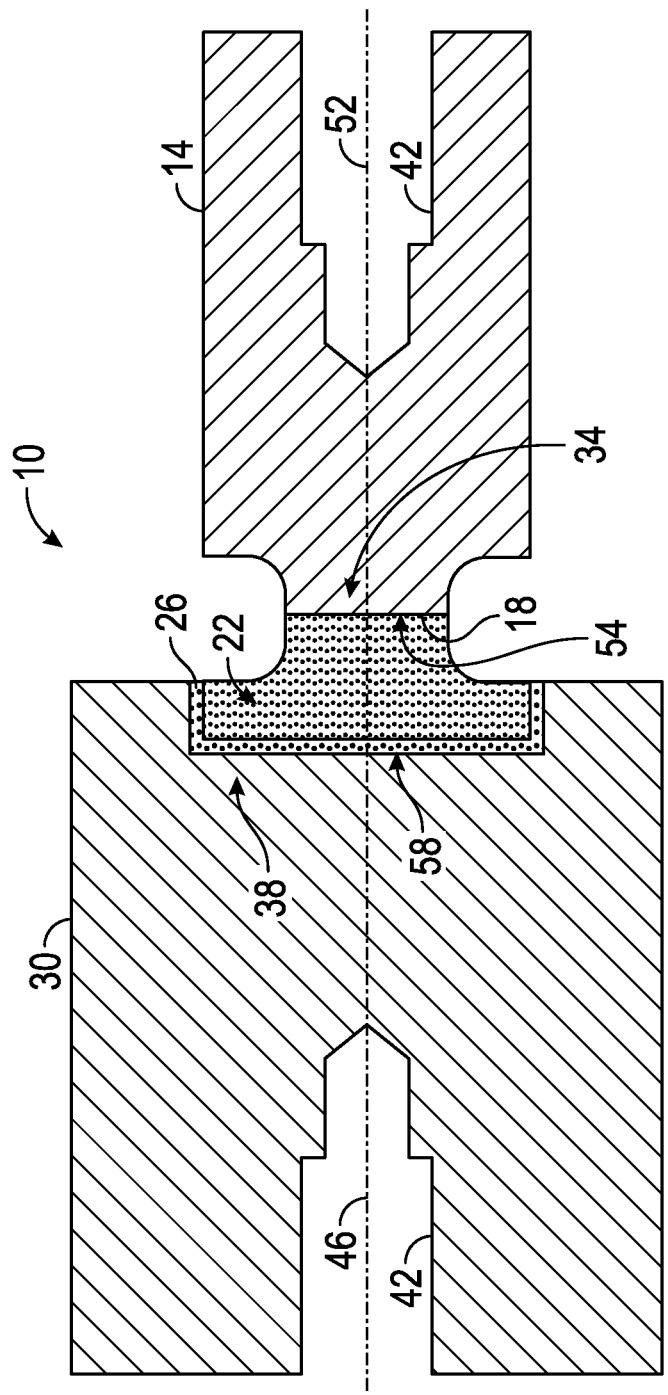
FIG. 1 depicts a side cross sectional view of a test specimen employed in a coating bond test method disclosed herein.

Referring to FIG. 1, an embodiment of a test specimen disclosed herein is illustrated at 10. The specimen 10 is used in an embodiment of a coating bond test method disclosed herein as will be described hereunder. The specimen 10 includes, a substrate 14 having a planar surface 18, a coating 22 bonded to the planar surface 18, an adhesive 26 adhered to the coating 22, and a pull-off bar 30 adhered to the adhesive 26. A first area 34 is defined by an interface between the substrate 14 and the coating 22 and has a value less than a second area 38 that is defined by an interface between the adhesive 26 and the coating 22.

The specimen 10 of the illustrated embodiment includes two engagement holes 42, with one being in the substrate 14 and the other being in the pull-off bar 30. The engagement holes 42 may be tapped with threads or have other features that enable a mandrel of a test machine (not shown) to be retained there within. Alternate methods of engaging the substrate 14 and the pull-off bar 30 to the machine are also contemplated. Such engagements allow the test machine to pull the substrate 14 away from the pull-off bar 30 in opposing directions that are essentially along a shared axis 46 of the pull-off bar 30 and the substrate 14 that is normal to the planar surface 18. The test machine monitors forces that are acting on the specimen 10. These forces are recorded at least until failure of the bond between the coating 22 and the planar surface 18 occurs. The stress at failure can be calculated by dividing the maximum force needed to cause the bond between the coating 22 and the planar surface 18 to fail by the first area 34.

The specimen 10 has advantages over those employed in other coating bond strength tests including ASTM-C633. ASTM-C633 calls for a specimen wherein an area between the coating and the substrate is the same as an area between the adhesive and the coating. It is not uncommon for samples tested in ASTM-C633 to fail at the adhesive-to-coating interface instead of the coating-to-substrate interface. Such a failure prevents determination of stress at the interface of interest which is the coating-to-substrate interface. The specimen 10 and methods disclosed herein, by setting the first area 34 be smaller than the second area 38, assures that the interface of interest, that is the interface between the coating 22 and the substrate 14 (at the planar surface 18) is where the bond failure occurs thereby providing useful data as to the actual strength of the bond in question, that is the bond of the coating 22 to the substrate 14.

The first area 34 can be made as small as is desired in relation to the second area 38. This area reduction allows the same tensile forces acting on both the adhesive 26 bonds (i.e. between the adhesive 26 and the coating 22 and the adhesive 26 and the pull-off bar 30) and the coating 22 bond (i.e. between the coating 22 and the substrate 14) to be distributed over the much smaller first area 34 and the larger second area 38. In so doing, a greater stress is applied to the coating bond than to the adhesive bonds. In an embodiment disclosed herein the first area 34 is reduced to a value that is less than half that of the second area 38. The first area 34 has a circular shape with a first diameter 54 of 0.4 inches while a second diameter 58 where the coating 22 is adhered to by the adhesive 26 is 1.0 inches. These diameters 54, 58 result in the first area 34 being 0.126 inches squared and the second area 38 being 0.785 inches squared. As such the ratio of the first area 34 to the second area 38 is just 0.16 or 16 percent. During fabrication of the test specimen 10, care should be taken to make the pull-off bar 30, the second area 38, the coating 22, and the end 74 (FIG. 2) all be concentric such that they are all centered on the centerline 52. Doing so assures that loading along the axis 46 results in a failure between the coating 22 and the substrate 14 being in tension only.

Figure 2:
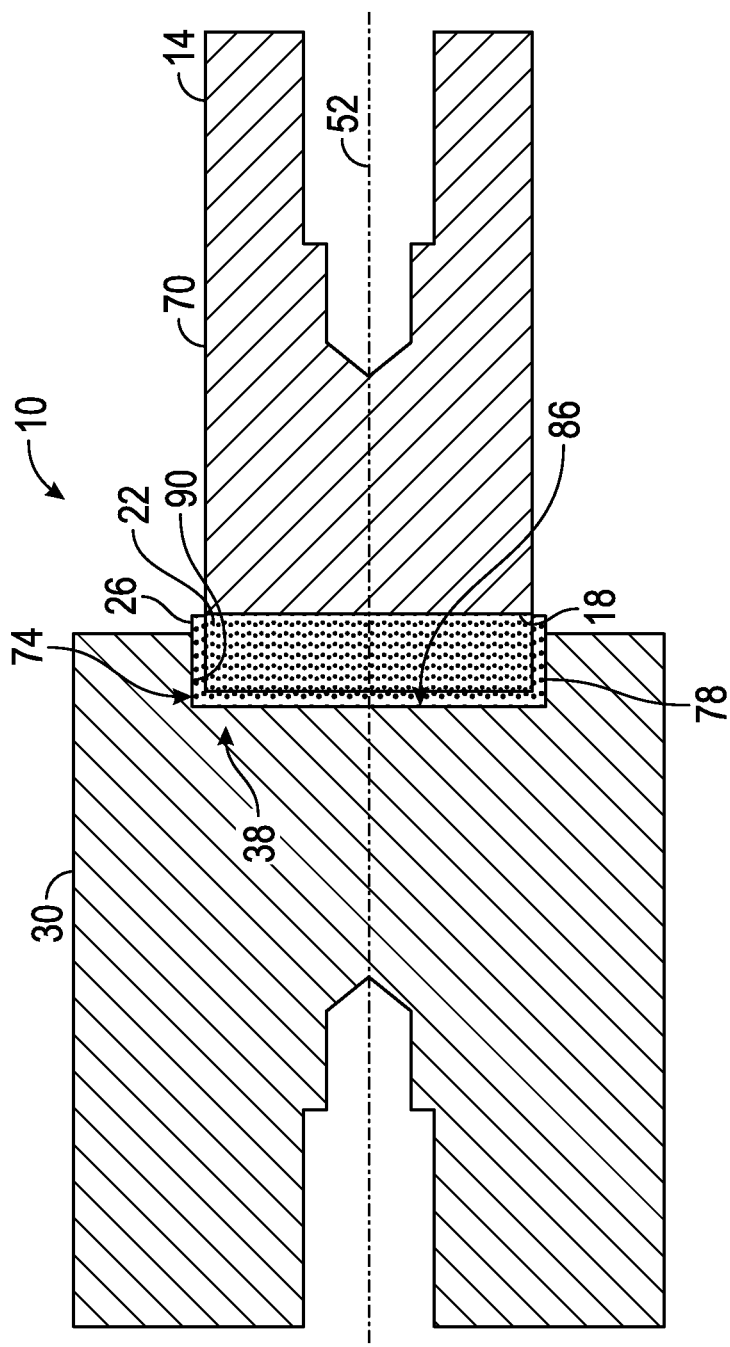
FIG. 2 depicts a side cross sectional view of a test specimen in a state prior to being ready for use in the coating bond test method disclosed herein.

Referring to FIG. 2, the specimen 10 in one embodiment is formed by first forming the substrate 14 into either a cylindrical or a rectangular member 70, with the planar surface 18 on one end 74 thereof perpendicular to a centerline 52 of the substrate 14. The coating 22 is then applied to the planar surface 18 in whatever method the particular coating 22 to be tested calls for. The coating 22 can be an existing coating, such as a thermal spray coating or a cold spray deposit, for example, or an entirely new coating for which the bond strength is sought. The adhesive 26 is applied and compressed between the coating 22 and a recess 78 formed in the pull-off bar 30. In one embodiment the recess 78 is made to be a circular depression in the pull-off bar 78 that is just slightly larger in diameter than the substrate 14. Any excess diameter of the coating 22 is removed such that the coating 22 has the same diameter as the substrate 14. As such the adhesive 26 is able to bond over the total second area 38 that includes not only a portion 86 of the recess 78 that is parallel to the planar surface 18 and thus is also loaded in tension normal to the planar surface 18 during a test, but also a radially inwardly facing portion 90 that is perpendicular to the planar surface 18 and is thus loaded in shear during a test. Compression of the adhesive 26 between the substrate 14 and the pull-off bar 30 while the adhesive 26 cures can help assure integrity of the bond provided by the adhesive 26. Elevated temperatures can also aid in curing of the adhesive 26.

Once the adhesive 26 is fully cured a portion of at least the substrate 14 and the coating 22 can be reduced to that of the first area 34 (FIG. 1). Alternatively, portions of the pull-off bar 30 and the adhesive 26 can also be removed during the reduction to that of the first area 34. This may be done by machining, or other methods of material removal, until the desired reduction in area is complete. Making the first area 34 round, as is done in the illustrated embodiment, can simplify the reduction process while making the finished specimen 10 easy to mount in a test machine and easy to apply a load symmetrically relative to the first area 34.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A coating bond test method, comprising:
    attaching with an adhesive a pull-off bar to a coating on a planar surface of a substrate for which a normal bond strength between the coating and the substrate is sought;
    reducing a first area defined by an interface between the substrate and the coating to a value less than a second area defined by an interface between the adhesive and the coating;
    urging the pull-off bar away from the substrate in a direction normal to the planar surface until failure occurs; and
    recording a load at which failure occurred.

2. The coating bond test method of claim 1, further comprising curing the adhesive.

3. The coating bond test method of claim 1, further comprising reducing the first area with machining.

4. The coating bond test method of claim 1, wherein at least a portion of the interface between the adhesive and the coating is parallel to the interface between the substrate and the coating.

5. The coating bond test method of claim 1, wherein at least a portion of the interface between the adhesive and the coating is perpendicular to the interface between the substrate and the coating.

6. The coating bond test method of claim 1, further comprising urging at least a portion of the attachment between the coating and the pull-off bar in shear.

7. The coating bond test method of claim 1, wherein the attaching includes compressing the adhesive between the pull-off bar and the coating while the adhesive cures.

8. The coating bond test method of claim 1, further comprising reducing the first area to less than half the second area.

9. The coating bond test method of claim 1, further comprising shaping the first area to have a round shape.

10. The coating bond test method of claim 1, further comprising calculating stress at which the failure occurred.

11. A method of making a specimen for testing bond strength of a coating, comprising:
    forming a substrate with a planar surface;
    applying a coating to the planar surface;
    attaching with adhesive a pull-off bar to the coating; and
    reducing a first area defined by an interface between the substrate and the coating to a value less than a second area defined by an interface between the adhesive and the coating.

12. The method of making a specimen for testing bond strength of a coating of claim 11, further comprising reducing the first area until it is less than half the second area.

13. The method of making a specimen for testing bond strength of a coating of claim 11, further comprising orienting at least a portion of the second area parallel to the planar surface.

14. The method of making a specimen for testing bond strength of a coating of claim 11, further comprising orienting at least a portion of the second area perpendicular to the planar surface.

15. The method of making a specimen for testing bond strength of a coating of claim 11, further comprising shaping at least the first area to be circular.

16. The method of making a specimen for testing bond strength of a coating of claim 11, further comprising concentrically aligning the substrate and the pull-off bar to assure the coating to planar surface interface is loaded in tension only when the substrate and pull-off bars are pulled away from one another along their shared axis.

* * * * *